US00PP28565P2

(12) United States Plant Patent
Ui et al.

(10) Patent No.: US PP28,565 P2
(45) Date of Patent: Oct. 24, 2017

(54) ***PETUNIA-CALIBRACHOA* HYBRID PLANT NAMED 'SAKPXC016'**

(50) Latin Name: ***Petunia-Calibrachoa* intergeneric hybrid**
Varietal Denomination: SAKPXC016

(71) Applicant: Sakata Seed Corporation, Yokohama (JP)

(72) Inventors: Akinobu Ui, Iwata (JP); Shin Ishikawa, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 14/999,134

(22) Filed: Mar. 31, 2016

(51) Int. Cl.
*A01H 5/02* (2006.01)

(52) U.S. Cl.
USPC ..... Plt./356.11

(58) Field of Classification Search
USPC ..... Plt./356.11
See application file for complete search history.

*Primary Examiner* — Annette Para
(74) *Attorney, Agent, or Firm* — Barbara Campbell; Bethany R. Roahrig; Cochran Freund & Young, LLC

(57) ABSTRACT

A new *Petunia-Calibrachoa* hybrid plant particularly distinguished by having pink flower color with darker pink veins and a yellow throat and a spreading plant habit, is disclosed.

2 Drawing Sheets

Genus and species: *Petunia-Calibrachoa* intergeneric hybrid.
Variety denomination: 'SAKPXC016'.

BACKGROUND OF THE NEW PLANT

The present invention comprises a new and distinct variety of *Petunia-Calibrachoa* (Petchoa) referred to by the variety name 'SAKPXC016'. 'SAKPXC016' originated from a hybridization in Kakegawa, Japan in December 2009 between the proprietary female *Petunia* line 'AM6-81A-1A-1A-1A' (unpatented) and the proprietary male *Calibrachoa* line '8B-43A-V1'.

In January 2010, an F1 generation from the initial hybridization was grown and approximately 41 seeds were obtained. In July 2010, 6 plants from the F1 generation of seeds were cultivated in a greenhouse. F1 plants exhibited pink and lavender flower colors with mounding and semi-mounding habits. In July 2010, a single plant was selected and designated 'K2011-J-120' which had pink flowers with a yellow eye color, vigorous blooming, and a mounding habit. In August 2010, the selection was first vegetatively propagated to produce rooted cuttings and plants of the selection were cultivated and evaluated in an open field. In November 2010, the selection was observed to have its distinctive characteristics remain stable. In December 2010, the selection was propagated again and plants were cultivated. In April 2011, 'K2011-J-120' was observed to have its distinct characteristics remain stable. 'K2011-J-120' was confirmed that the distinct characteristics of the plant were fixed and stable. All breeding work was conducted at the Kakegawa research station in Kakegawa, Japan. 'K2011-J-120' was later named 'SAKPXC016' and was found to reproduce true to type in successive generations of asexual propagation via vegetative cuttings in Salinas, Calif.

SUMMARY

The following are the most outstanding and distinguishing characteristics of this new variety when grown under normal horticultural practices in Salinas, Calif.

1. Pink flower color with darker pink veins and a yellow throat; and
2. A spreading plant habit.

DESCRIPTION OF THE PHOTOGRAPHS

This new *Petunia-Calibrachoa* plant is illustrated by the accompanying photographs which show the plant's overall plant habit including form, foliage, and flowers. The photographs are of a plant grown in Salinas, Calif. under greenhouse conditions. The colors shown are as true as can be reasonably obtained by conventional photographic procedures.

DESCRIPTION OF THE NEW VARIETY

Figure 1:
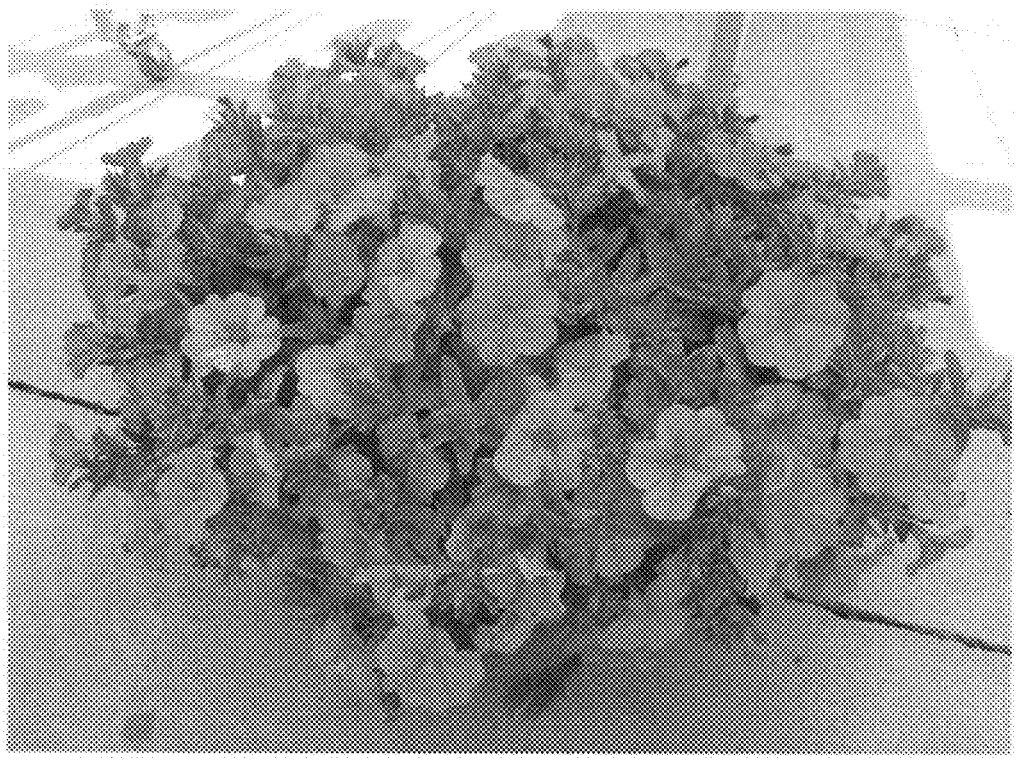
FIG. 1 shows the overall plant habit of the plant grown in a pot.
Figure 2:
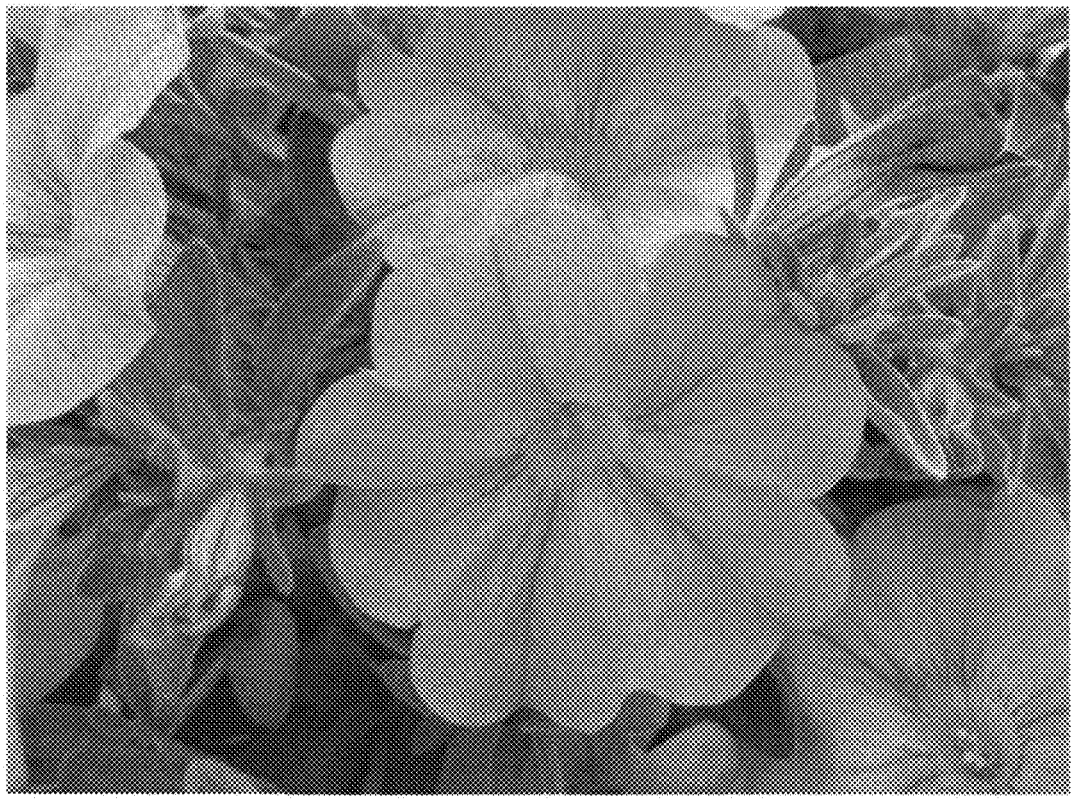
FIG. 2 shows a close-up of the foliage, buds, and flower.

The following detailed descriptions set forth the distinctive characteristics of 'SAKPXC016'. Color references are to The R.H.S. Colour Chart of The Royal Horticultural Society of London (R.H.S.), 4$^{th}$ edition. Anatomic labels are from *The Cambridge Illustrated Glossary of Botanical Terms*, by M. Hickey and C. King, Cambridge University.

Classification:

*Family*.—Solanaceae.
*Botanical*.—*Petunia-Calibrachoa* hybrid.
*Common*.—Petchoa, *petunia-calibrachoa*.
*Designation*.—'SAKPXC016'.

Growth:

*Environmental conditions for plant growth*.—The terminal 1.0 to 1.5 inches of an actively growing stem was excised. The vegetative cuttings were propagated in five to six weeks. The base of the cuttings were dipped for 1 to 2 seconds in a 1:9 solution of DIP 'N GROW (1 solution: 9 water), a root inducing solution, immediately prior to sticking into the cell trays. Cuttings were stuck into plastic cell trays having 98 cells, and containing a moistened peat moss-based growing medium. For the first week, the cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Parentage:

*Female parent*.—The proprietary *Petunia* line 'AM6-81A-1A-1A-1A' (unpatented).

*Male parent*.—The proprietary *Calibrachoa* line '8B-43A-V1' (unpatented).

Plant description:

*Habit*.—Mounding.

*Height*.—20.0 cm from the soil line to the top of the foliage.

*Spread*.—60.0 cm.

*Life cycle*.—Tender perennial.

*Time and conditions to produce a rooted cutting*.—4 weeks.

*Time to bloom from propagation*.—8 to 10 weeks.

*Flowering requirements*.—Will flower so long as day length is greater than 12 hours and temperature exceeds 13° C.

Stems:

*Color*.—RHS 144A (Yellow-Green).

*Anthocyanin color*.—Absent.

*Pubescence*.—Moderate.

*Pubescence color*.—RHS N155A (White).

*Description*.—Dull, circular in cross-section.

*Stem diameter*.—4.0 mm for the main stems/branches; 2.0 mm for the secondary branches/stems.

*Stem length*.—Length of entire stem from end to end to 18.0 cm; length from the soil line to the first node is 1.0 cm.

*Internode length*.—2.0 cm.

Leaves:

*Arrangement*.—Alternate.

*Shape*.—Elliptic.

*Apex*.—Obtuse.

*Base*.—Attenuate.

*Margin*.—Entire.

*Surface appearance*.—Dull.

*Length*.—5.0 cm.

*Width*.—2.0 cm.

*Color*.—Upper surface: RHS 137B (Green). Lower surface: RHS 138B (Green).

*Fragrance*.—Absent.

*Surface pubescence*.—Light pubescence.

*Pubescence color*.—RHS N155A (White).

*Petiole*.—Absent.

*Venation pattern*.—Pinnate.

Flowers:

*Total number of flowers per plant*.—Approximately 110.

*Inflorescence type*.—Solitary.

*Flowering habit*.—Indeterminate.

*Duration of flower life on the plant*.—5 days.

*Shape*.—The flowers are funnel shaped with five fissures and a shallow, yet prominent, indentation of the petal tip at the mid-vein.

*Flower diameter*.—6.0 cm.

*Flower depth*.—0.5 cm.

*Corolla*.—Composed of 5 petals, fused.

*Petals*.—Shape: Bilabiate, fused, margin cleaved. Length: 3.0 cm. Width: 2.4 cm. Apex: Truncate. Margin: Entire. Pubescence: Glabrous. Color: Upper lobes: Closest to but brighter than RHS N74A (Red-Purple) with RHS 12A (Yellow) eye. Lower lobes: RHS N74C (Red-Purple).

*Corolla tube, inner surface color*.—Closest to RHS 12A (Yellow).

*Corolla tube, outer surface color*.—RHS 4C (Yellow) with RHS 144C (Yellow-Green) veins.

*Flower tube length*.—2.5 cm.

*Flower tube diameter*.—1.0 cm.

*Flower tube pubescence*.—Absent in the inner surface and slight on the outer surface.

Calyx:

*Form*.—Composed of 5 sepals, fused below the middle.

*Sepal*.—Shape: Elliptical. Apex: Obtuse. Margin: Entire. Length: 2.5 cm. Diameter: 1.0 mm. Color: Upper surface: RHS 138A (Green). Lower surface: RHS 138A (Green).

Bud:

*Surface texture*.—Pubescent.

*Length*.—3.2 cm.

*Diameter*.—0.8 cm.

*Shape*.—Ovate.

*Color*.—RHS N81B (Purple-Violet) with RHS N77A (Purple) veins.

Peduncle:

*Length*.—2.5 cm.

*Diameter*.—1.0 mm.

*Color*.—RHS 144 A (Yellow-Green) with very slight anthocyanin on some, anthocyanin color is RHS N187A (Greyed-Purple).

*Surface texture and appearance*.—Dull, moderate pubescence, pubescence color is RHS N155A (White).

Reproductive organs:

*Ovary*.—Superior.

*Placenta arrangement*.—Central.

*Pistil number*.—1 per flower.

*Pistil length*.—1.6 cm.

*Stigma color*.—RHS 143C (Green).

*Style length*.—1.5 cm.

*Style color*.—RHS 145C (Yellow-Green).

*Stamens number and form*.—5, free.

*Stamen length*.—1.0 cm.

*Stamen color*.—RHS 154 D (Yellow-Green).

*Filament color*.—RHS 11B (Yellow).

*Pollen color*.—RHS 12A (Yellow).

*Fragrance*.—Absent.

Seed production: None observed.

Environmental conditions, disease and insect resistance: Excellent resistance to rain, heat and drought. Will not tolerate temperatures below 10° C. Plants are susceptible to *Botrytis*, powdery mildew, various stem and root rots, and certain viruses, like Tobacco Mosaic Virus and Impatiens Necrotic Spotted Virus. Plants can be infested with aphids, leafminer, whitefly and various *Lepitopdera*.

COMPARISON WITH PARENTAL LINES AND KNOWN VARIETY

'SAKPXC016' is distinguished from its parents as shown in Table 1.

TABLE 1

Comparison with Parental Lines

| Characteristic | 'SAKPXC016' | Female Parent 'AM6-81A-1A-1A-1A' | Male Parent '8B-43A-V1' |
|---|---|---|---|
| Flower color | Deeper coloration of pink than parental lines with yellow eye | Pink with yellow eye | Lavender |
| Plant growth habit | Mounding with more branching than parental lines | Mounding | Compact |

When 'SAKPXC016' is compared to the commercial variety 'Kakegawa S84' (U.S. Plant Pat. No. 18,698), the following differences as described in Table 2.

TABLE 2

Comparison with Similar Variety

| Characteristic | 'SAKPXC016' | 'Kakegawa S84' |
|---|---|---|
| Petal color, upper surface | Closest to but brighter than RHS N74A (Red-Purple) with RHS 12A (Yellow) eye | RHS 73B (red-purple) |
| Petal color, lower surface | RHS N74C (Red-Purple) | RHS N155A (white) |
| Plant growth habit | Mounding | Mounding |

We claim:

1. A new and distinct cultivar of *Petunia-Calibrachoa* hybrid plant as illustrated and described herein.

* * * * *